(12) United States Patent
Mouchawar et al.

(10) Patent No.: US 6,628,986 B1
(45) Date of Patent: Sep. 30, 2003

(54) SYSTEM FOR PREDICTING DEFIBRILLATION THRESHOLD BASED ON PATIENT DATA

(75) Inventors: Gabriel A. Mouchawar, Valencia, CA (US); David W. Adinolfi, Eden Prairie, MN (US); Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/981,573

(22) Filed: Oct. 16, 2001

Related U.S. Application Data

(63) Continuation of application No. 09/500,113, filed on Feb. 8, 2000, now Pat. No. 6,345,200.

(51) Int. Cl.$^7$ ................................................. A61N 1/39
(52) U.S. Cl. ............................................................... 607/8
(58) Field of Search ............................... 607/1–8, 72, 74, 607/30–32, 59–60; 600/300–301, 508; 128/906, 920, 923

(56) References Cited

U.S. PATENT DOCUMENTS

| | | | | |
|---|---|---|---|---|
| 3,862,636 A | * | 1/1975 | Bell et al. | 607/17 |
| 4,574,810 A | * | 3/1986 | Lerman | 607/8 |
| 5,350,403 A | * | 9/1994 | Stroetmann et al. | 607/5 |
| 5,531,770 A | * | 7/1996 | Kroll et al. | 607/8 |
| 5,709,711 A | * | 1/1998 | Fain | 607/8 |
| 5,720,767 A | * | 2/1998 | Amely-Velez | 607/5 |
| 6,351,675 B1 | * | 2/2002 | Tholen et al. | 607/59 |

OTHER PUBLICATIONS

Kroll, Mark W., et al., Implantable Cardioverter Defibrillator Therapy, The Engineering–Clinical Interface, Kluwer Academic Publishers Group, pp 63–129 (1996).

Shahidi, A.V. et al, *A Three–Dimensional Heart–Torso Model for Cardiac Defibrillation*, pp. 649–650; Guan, B. et al, *Comparison Study of Different Numerical Methods on 3–D Human Thorax Finite Element Models*, pp. 651–652; Blilie, D.E. et al, *Generation of an Anatomically Correct Human Thorax Finite Element Model*, pp. 653–654, Proceedings of the 14$^{th}$ Annual International Conference of the IEEE Engineering in Medicine and Biology Society Paris–France Pt 2 of 7 (Oct. 29–Nov. 1, 1992).

Khalighi, K., MD et al, *Clinical Predictors of Transvenous Defibrillation Energy Requirements*, The American Journal of Cardiology, Vol 79, pp. 150–153 (Jan. 15, 1997).

Neuzner, J. MD et al, *Clinical Predictors of Defibrillation Energy Requirements*, The American Journal of Cardiology, Vol 79, pp. 205–206 (Jan. 15, 1997).

Smits, K. et al *Effect of Subcutaneous Electrode Design and Location on Defibrillation Current Density Distribution in an Inhomogenous Computer Model*, PACE, Vol 16, Pt II, pp. 253 (May 1993).

Jorgenson, D.B. et al *Toward Predicting Defibrillation Efficacy for Clinical Lead Systems on a Patient–Specific Basis from Thoracic CT Data and Finite Element Analysis*, Circulation Vol 90, Pt 2, p. 0945 (Oct. 1994).

* cited by examiner

*Primary Examiner*—Kennedy Schaetzle
*Assistant Examiner*—Kristen Droesch

(57) ABSTRACT

The implant guiding programmer is configured to automatically determine a defibrillation threshold (DFT) for a particular patient and to further determine an optimal implantation configuration for an implantable cardioverter fibrillator (ICD). In one implementation, to determine the DFT for the patient, the programmer correlates patient specific data with a predictive data base containing DFT information for an entire population of patients. The programmer additionally determines an optimal implantation configuration for the patient, wherein the optimal configuration is one which is capable of exceeding the DFT for the patient using minimal electrical pulse energy.

20 Claims, 8 Drawing Sheets

| PARAMETER | ADJUSTMENT FACTORS FOR APPLYING TO AVERAGE DFT |
|---|---|
| AGE | AGE SPECIFIC FACTORS |
| GENDER | GENDER SPECIFIC FACTORS |
| MEDICAL HISTORY | MED. HISTORY SPEC. FACTORS |
| HEART SIZE | HEART SIZE SPEC. FACTORS |
| CHEST SIZE | CHEST SIZE SPEC. FACTORS |
| LEFT VENTRICULAR MASS | LVM SPECIFIC FACTORS |
| ⋮ | ⋮ |

FIG. 3 — DFT PREDICTION DATABASE

| IMPLANTATION CONFIGURATION | CONFIGURATION PARAMETERS |
|---|---|
| CONFIG. #1: ICD MODEL I, LEAD TYPE: NON-THORACOTOMY, POLARITY POSITIVE, NO AUXILIARY WIRE | PROGRAMMABLE THRESHOLDS; COSTS; EXPECTED LONGEVITY; ELECTRICAL ENERGY PER PULSE; ETC |
| CONFIG. #2: ICD MODEL I, LEAD TYPE: EPICARDIAL POLARITY POSITIVE, NO AUXILIARY WIRE | PROGRAMMABLE THRESHOLDS; COSTS; EXPECTED LONGEVITY; ELECTRICAL ENERGY PER PULSE; ETC |
| ⋮ | ⋮ |

FIG. 6 — ICD IMPLANTATION CONFIGURATION DATABASE

SYSTEM FOR PREDICTING DEFIBRILLATION THRESHOLD BASED ON PATIENT DATA

CROSS-REFERENCE TO RELATED APPLICATIONS

This application is a continuation of U.S. patent application Ser. No. 09/500,113, filed Feb. 8, 2000, now U.S. Pat. No. 6,345,200.

FIELD OF THE INVENTION

The invention generally relates to implantable cardioverter defibrillators (ICD's)and in particular to techniques for determining and setting defibrillation thresholds for use with ICD's.

DESCRIPTION OF RELATED ART

An ICD is an implantable medical device capable of detecting the onset of ventricular fibrillation, or related arrhythmias, and for administering a defibrillation electrical pulse directly to the heart tissue to terminate the fibrillation. Preferably, the ICD is configured to discharge the minimum amount of electrical energy necessary to reliably defibrillate the heart. The amount of energy discharged in a single defibrillation pulse is the "defibrillation dosage". By keeping the defibrillation dosage to a minimum: possible injury to the heart tissue caused by the electrical pulse is avoided; there is less discomfort to the patient after the patient has been revived; and the longevity of the power supply of the ICD is enhanced.

The defibrillation dosage must be sufficient to generate an "actual defibrillation voltage" in the heart of the patient sufficient to overcome a threshold "tissue defibrillation voltage" of the patient. The tissue defibrillation threshold is the minimum electrical voltage gradient that must be induced within the muscle tissue of the heart to reliably defibrillate the tissue. The tissue defibrillation threshold is typically about five volts per centimeter but can vary depending upon the characteristics of the heart, particularly the extent to which the tissue of the heart has been damaged by previous incidents of fibrillation or other arrhythmias.

The actual defibrillation voltage induced in the heart from a defibrillation pulse depends upon: the strength of the pulse generated by the ICD; the configuration of the ICD and its components, particularly the size, type and location of the leads of the ICD; and the physical characteristics of the heart and thorax of the patient, particularly the size and shape of the heart, the size and shape of the thorax, and the amount of fat present in the thorax. Accordingly, a particular defibrillation dosage administered by an ICD can result in significantly different actual defibrillation voltages within the heart tissue depending upon characteristics of the patient and upon the configuration of the ICD implanted in the patient.

Additional information regarding defibrillation dosages and thresholds may be found in chapters 4 and 5 of "Implantable Cardioverter Defibrillator Therapy—The Engineering—Clinical Interface," edited by Mark W. Kroll and Michael H. Lehmann, Kluwer Academic Publishers (1996).

As noted, it is desirable to minimize the defibrillation dosage administered by the ICD. Hence, it is desirable to first determine an optimal implantation configuration for the ICD and its components which achieves the highest actual defibrillation voltage within the heart tissue using the lowest defibrillation dosage. The optimal configuration also minimizes overall costs and maximizes ICD longevity. The optimal configuration is one that not only specifies the components to be used, including the make and model of the ICD, the leads etc., but also specifies location in which each component is to implanted. The optimal configuration is, of course, preferably determined prior to implantation of the ICD and its components into the patient.

Heretofore, unfortunately, there has been no expedient, reliable and inexpensive noninvasive technique for determining the optimal ICD implantation configuration for a particular patient. As a result, the physician may erroneously select an implantation configuration which requires that the ICD discharge unnecessarily large amounts of electrical energy within each defibrillation pulse, thereby possibly damaging heart tissue, reducing the longevity of the ICD and increasing the amount of pain the patient experiences after being revived. A non-optimal implantation configuration may also result in greater costs and overall discomfort to the patient, particularly if a large and expensive ICD is implanted, when a smaller and less expensive one would be sufficient if implanted using an optimal configuration of leads, auxiliary wires, and the like.

Thus, it would be highly desirable to provide an improved technique for determining an optimal ICD implantation configuration—specifying the components to be used and the location in which each component is to implanted—based on the characteristics of a particular patient. It is to this end that aspects of the invention directed.

Once an ICD and its peripheral components have been selected and implanted, the defibrillation dosage of the ICD must be set to an amount sufficient to reliably defibrillate the heart, i.e. the defibrillation dosage must be set to an amount sufficient to achieve an actual defibrillation voltage gradient within the heart tissue exceeding the tissue defibrillation threshold. Herein, the minimum ICD defibrillation dosage sufficient to reliably defibrillate the heart is referred to as the "dosage defibrillation threshold" or DFT. Typically, the DFT is a programmable parameter of the ICD. In use, if ventricular fibrillation is detected, the ICD initially attempts to defibrillate the heart using a defibrillation dosage set to the DFT. If ventricular fibrillation is not terminated using pulses at the DFT, the ICD generates one or more additional pulses of higher dosage, typically using the maximum energy available.

As noted above, it is desirable to employ the lowest defibrillation dosage possible to reliably defibrillate the heart. Hence, the optimal setting for programming the DFT of the ICD is the lowest DFT value sufficient to achieve reliable defibrillation, which, as also noted, can depend greatly on the characteristics of the patient, such as the shape and size of the heart and thorax, and on the configuration of the ICD and its components. Thus, the optimal value may vary greatly from patient to patient and, for a particular patient, may vary greatly depending upon the ICD implantation configuration. Unfortunately, heretofore, there has been no reliable, inexpensive and expedient technique for accurately determining the optimal value for programming the DFT of an ICD based upon the characteristics of the patient and upon the ICD implantation configuration.

Conventionally, to program the DFT of an ICD, ventricular fibrillation is induced within the patient, then a series of defibrillation pulses of differing dosages are administered to the heart in an attempt to terminate the fibrillation. The DFT is then programmed to the lowest dosage level that terminated fibrillation, plus some safety margin. In one technique, fibrillation is repeatedly induced and pulses are output with decreasing dosage levels until the dosage level is insufficient to terminate the fibrillation. In another technique, a binary search pattern is employed whereby fibrillation is repeatedly induced, and then defibrillation pulses alternating between high and low output dosages are administered with a voltage differential between the high and low pulses incrementally reduced until an approximate DFT is identified.

Although these techniques have been found to be effective, considerable room for improvement remains. First, once fibrillation is induced, there is a risk that the physician will not be able to subsequently terminate the fibrillation, resulting in loss of life to the patient. Second, the sequence of defibrillation pulses may further injure the cardiac tissue of the patient and certainly can be painful to the patient. Moreover, the overall process typically takes several hours resulting in significant costs. Typically, the ICD itself is employed to administer the electrical defibrillation shocks and, if a relatively large number of shocks are required to determine the DFT, the power supply of the ICD can be depleted considerably during the determination process. If relatively few test defibrillation pulses are used, then the technique can only approximate the correct DFT thereby requiring the physician to set the DFT of the ICD using a high safety margin which, in turn, can ultimately reduce the longevity of the power source of the ICD.

Thus, in addition to providing an improved technique for determining an optimal ICD implantation configuration, it would be desirable to also provide an improved technique for determining the optimal DFT for programming an ICD which reduces the number of times that fibrillation needs to be induced in the patient, reduces the number and magnitude of electrical pulses administered to the heart of the patient during the determination process, and permits the DFT to be determined more precisely than many conventional techniques permit. It is to these ends that other aspects of the present invention are directed.

Hence, certain aspects of the invention are directed to determining an optimal ICD implantation configuration for a particular patient and then for determining the optimal DFT for programming the ICD. Other aspects of the invention are directed to determining the optimal DFT based upon a pre-determined ICD configuration. Such is particularly useful if an ICD has already been implanted in a patient. Still other aspects of the invention are directed to determining a suitable DFT for use with a patient based upon characteristics of the patient. Still other aspects of the invention are directed to determining whether a particular ICD configuration is acceptable for use with a patient given a predetermined DFT for the patient.

SUMMARY OF THE INVENTION

In accordance with a first aspect of the invention, a method is provided for determining the DFT for a patient. In accordance with the method, predictive information correlating patient clinical data with tissue defibrillation thresholds is maintained. Patient data for a particular patient is then received. The defibrillation threshold for the particular patient is automatically determined based upon the data input for the patient in combination with the predictive information correlating patient clinical data with tissue defibrillation thresholds.

In an exemplary embodiment, the predictive information correlating patient clinical data with DFT includes one or more of gender vs. threshold, ventricular fibrillation history vs. threshold, heart size vs. threshold, chest size vs. threshold, left ventricular mass vs. threshold, atrial mass vs. threshold, and medication usage vs. threshold, ejection fraction vs. threshold, NY classification vs. threshold. Patient data input for the patient includes corresponding information such as the gender of the patient, any history of ventricular fibrillation in the patient, the heart size, left ventricular mass, atrial mass, chest size of the patient, and any medications expected to be used by the patient.

Preferably, the patient clinical data is input into, and maintained within, an ICD programmer used in connection with programming the ICD. The patient clinical data is arranged in a set of tables which correlate DFT with various ranges of the aforementioned groups of patient clinical data, such as gender, chest size, atrial and ventricular mass, and the like. The parameters for the patient under consideration is then input by a physician or other medical personnel into the programmer which automatically applies the patient data to the predictive information stored within the tables and determines therefrom the expected DFT for the patient, which can then be displayed using a display screen of the programmer for use by the physician in determining an optimal implantation configuration for the ICD, including the setting of any programmable DFT parameters of the ICD.

In accordance with a second aspect to the invention, a method for determining the DFT for a particular patient based upon images of the thorax of the patient is provided. In accordance with the method, the thorax is imaged, using MRI or similar technique, then the thorax of the patient is modeled based upon the images of the patient to generate a patient model. Conduction characteristics of electrical pulses in the patient are determined based upon the patient model. Then, the DFT for the patient is determined based upon the conduction characteristics.

In an exemplary embodiment, the thorax of the patient is modeled, in part, by employing finite element analysis to extract the shape and boundary of various structures in the thorax, including the individual chambers of the heart and the major arteries and veins in the vicinity of the heart and possibly further including the lungs, the rib cage, the sternum, any fat disposed in the vicinity of the heart, thoracic muscles and cutaneous fat. Once the structure boundaries are determined, an electrical conductivity value is assigned to each structure boundary, then differential equations representative of electrical conduction characteristics are solved to estimate the electrical field strength, current density, or electrical potential within the heart of the patient. The DFT is then determined based upon the estimates of the electrical field strength, the current density, or the electrical potential. Thus, in the exemplary embodiment, the DFT for the patient is determined directly from images generated of the thorax of the patient using modeling techniques.

Thus, in accordance with either the first or second aspects of the invention, the DFT for a patient is determined without having to repeatedly trigger fibrillation within the heart of the patient, then administer shocks of differing dosages in an attempt to terminate fibrillation. If desired, techniques drawn from both the first and second aspects of the invention can be combined to yield an even more reliable determination of the DFT for the patient. Also, although the techniques of the first and second aspects of the invention eliminate the need to defibrillate a patient to determine the tissue defibrillation threshold, it may nevertheless be desirable to defibrillate the patient at least once using the threshold that has been determined, to verify that the threshold is correct. It may also be desirable to utilize a safety margin as well in connection with the DFT to further ensure reliable defibrillation. The safety margin will likely be less than that which would be employed in connection with a defibrillation threshold determined using conventional techniques.

In accordance with a third aspect of the invention, a method is provided for determining an implantation configuration capable of achieving a DFT for an ICD to be implanted within a patient. In accordance with the method, predictive information correlating ICD implantation configurations with tissue defibrillation thresholds for a population of patients is maintained. The DFT for a particular patient is then input or otherwise determined. Then, an implantation configuration capable of providing defibrillation pulses achieving the DFT is automatically determined based upon the threshold for the particular patient in combination with the predictive information correlating ICD implantation configurations with defibrillation thresholds.

In an exemplary embodiment, the predictive information correlating ICD implantation configuration with tissue defibrillation thresholds includes one or more of lead type, lead position, ICD position, lead polarity, auxiliary wire positioning, and the amount of energy the ICD can provide in a single defibrillation pulse and the extend to which the ICD is programmable.

Preferably, the programmer further identifies an optimal implantation configuration. The programmer may, for example, identify the configuration requiring the least amount of energy to be generated by the ICD to achieve the DFT. Alternatively, the programmer may identify the configuration providing the lowest overall costs while also being capable of achieving the DFT. As another example, the programmer may identify the configuration providing the greatest device longevity while also being capable of achieving the DFT. As can be appreciated, the optimal configuration can be defined in a number of ways and, preferably, the programmer displays information identifying various configurations satisfying different optimal criteria.

Thus, various techniques are provided for determining the DFT for a particular patient and for automatically determining an acceptable, or perhaps optimal, implantation configuration sufficient to meet the DFT to ensure that the threshold is reliably met in the event fibrillation occurs within the patient. Hence, fibrillation need not be repeatedly induced within the patient and the patient need not be repeatedly shocked to terminate fibrillation. Accordingly, costs, risks and dangers inherent with those procedures are substantially eliminated. Numerous other advantages and features of the invention are also described herein. Apparatus embodiments of the invention are also provided.

BRIEF DESCRIPTION OF THE DRAWINGS

FIGS. 1–6 illustrate a method for determining a DFT for use with a particular patient and for subsequently determining an optimal implantation configuration, wherein both determinations are made using predictive databases incorporating data drawn from an entire population of patients and wherein:

FIG. 1 provides an overview of the method which automatically determines the DFT for a patient then automatically determines an optimal ICD implantation configuration based on the DFT;

FIG. 2 illustrates the method of automatically determining the DFT using a threshold prediction database;

FIG. 3 illustrates the threshold prediction database;

FIG. 4 illustrates a method of updating the threshold prediction database;

FIG. 5 illustrates the method for automatically determining the optimal implantation configuration using a configuration database; and FIG. 6 illustrates the implantation configuration database.

FIGS. 7–9 illustrate a method for determining an optimal implantation configuration and a DFT for use with the optimal configuration wherein the determinations are made by modeling the thorax of the patient to determine electrical conduction characteristics of the patient and wherein:

FIG. 7 provides an overview of the method;

FIG. 8 illustrates specific steps directed to the automatic determination of the optimal configuration; and FIG. 9 illustrates specific steps directed to determining effective electrical current or voltage in the heart of a patient based upon a model of the thorax of the patient.

DETAILED DESCRIPTION OF THE INVENTION

Referring first to the method of FIGS. 1–6, FIG. 1 provides an overview of the method for automatically determining a DFT using a predictive database and then for subsequently automatically determining an optimal implantation configuration for an ICD. Initially, at step 100, the programmer inputs data for the patient in which the ICD is to be implanted. The data includes one or more of the age, gender, medical history, heart size, chest size, left and right ventricular mass, atrial mass, ejection fraction, New York (N.Y.) Heart Association Classification of the patient, and any current medications prescribed to the patient. Preferably, all of these types of patient data are input. However, all are not necessarily required. The more data that is available, however, the more precise the subsequent determination of the DFT for use with the patient. The data may be input to the programmer manually by a physician or other medical personnel operating the programmer based upon information provided in patient records and the like. Alternatively, the information may be directly input into the programmer, perhaps from a centralized server maintaining information on numerous patients, including the particular patient under consideration.

At step 102, the programmer then applies the data that had been input at step 100 to a DFT prediction database to estimate the DFT for the particular patient using a technique described below in connection with FIGS. 2–3. At step 104, the programmer then displays the DFT for review by the physician. At step 106, the programmer inputs from the physician criteria for determining an optimal implantation configuration. Exemplary optimization criteria include lowest overall cost to the patient, greatest device longevity, or lowest amount of energy needed to be discharged by the ICD to meet the DFT. The lowest overall cost includes the cost of the ICD and its various components as well as costs associated with implanting the ICD and its components and long term costs associated with maintaining the ICD.

After the physician has selected one of the optimization criteria using a display screen of the programmer, the programmer then proceeds to automatically determine, at step 108, the optimal configuration consistent with the optimization criteria using a technique employing a predictive configuration database described below in connection with FIGS. 4–6. In addition to identifying the optimal configuration, within step 108 the programmer also identifies various acceptable implantation configurations. The acceptable and optimal configurations are displayed to the physician such that the physician may then select a configuration for actually implanting within the patient.

Figure 1:
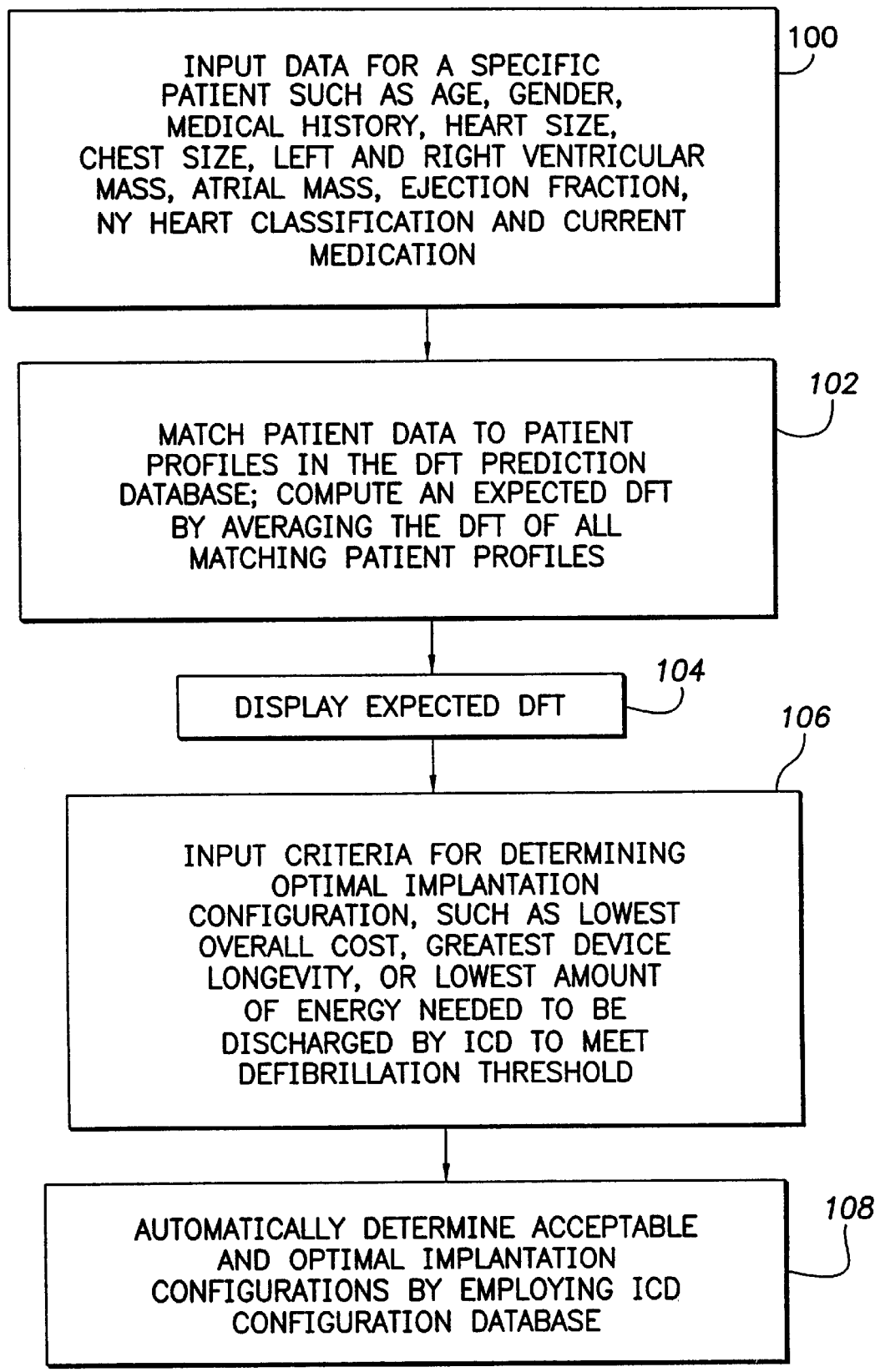

Thus, FIG. 1 illustrates a method for automatically determining a DFT without the need to repeatedly fibrillate, then defibrillate the patient as in typical conventional techniques. Hence, the significant risks and substantial costs described above are completely avoided. Moreover, depending upon the amount and accuracy of the patient data input by the physician and depending upon the accuracy of the DFT prediction database, the DFT can be determined much more precisely and reliably than conventional techniques which merely approximate the threshold using some number of iterations of a fibrillation/defibrillation process.

Moreover, once the DFT has been determined, the programmer further identifies optimal and acceptable implantation configurations sufficient to meet the threshold. Hence, prior to implantation of the ICD and its components, an optimal configuration providing, for example, reduced costs or increased longevity or both is determined. Thus, the physician need not bother trying to determine the optimal configuration based upon an analysis of technical information provided by ICD manufacturers and the physician can avoid erroneously implanting an ICD which may be too expensive than necessary, or which may lack necessary longevity, or which may simply not be sufficient to meet the DFT for the particular patient. Hence, costs are minimized and the need to explant an ICD that is not adequate for the patient is substantially avoided.

The physician should, of course, independently review the DFT determined by the programmer and the optimal implantation configuration identified by the programmer to verify that no obvious errors have been made by the programmer. Assuming that the DFT and the optimal implantation configuration are acceptable to the physician and to the patient, the physician then implants the ICD and auxiliary components into the patient and programs the ICD using the programmer to the DFT previously determined by the programmer. Preferably, the physician then conducts one defibrillation test wherein fibrillation is induced in the patient to verify that the ICD correctly detects the fibrillation and administers a defibrillation pulse sufficient to terminate the fibrillation. Thus, a single instance of fibrillation is induced merely to verify that the ICD is working properly and that the threshold is set properly. This is in contrast to the repeated cycles of fibrillation and defibrillation required using certain conventional techniques to identify the DFT. Accordingly, costs and risks to the patient are further reduced.

Figure 4:
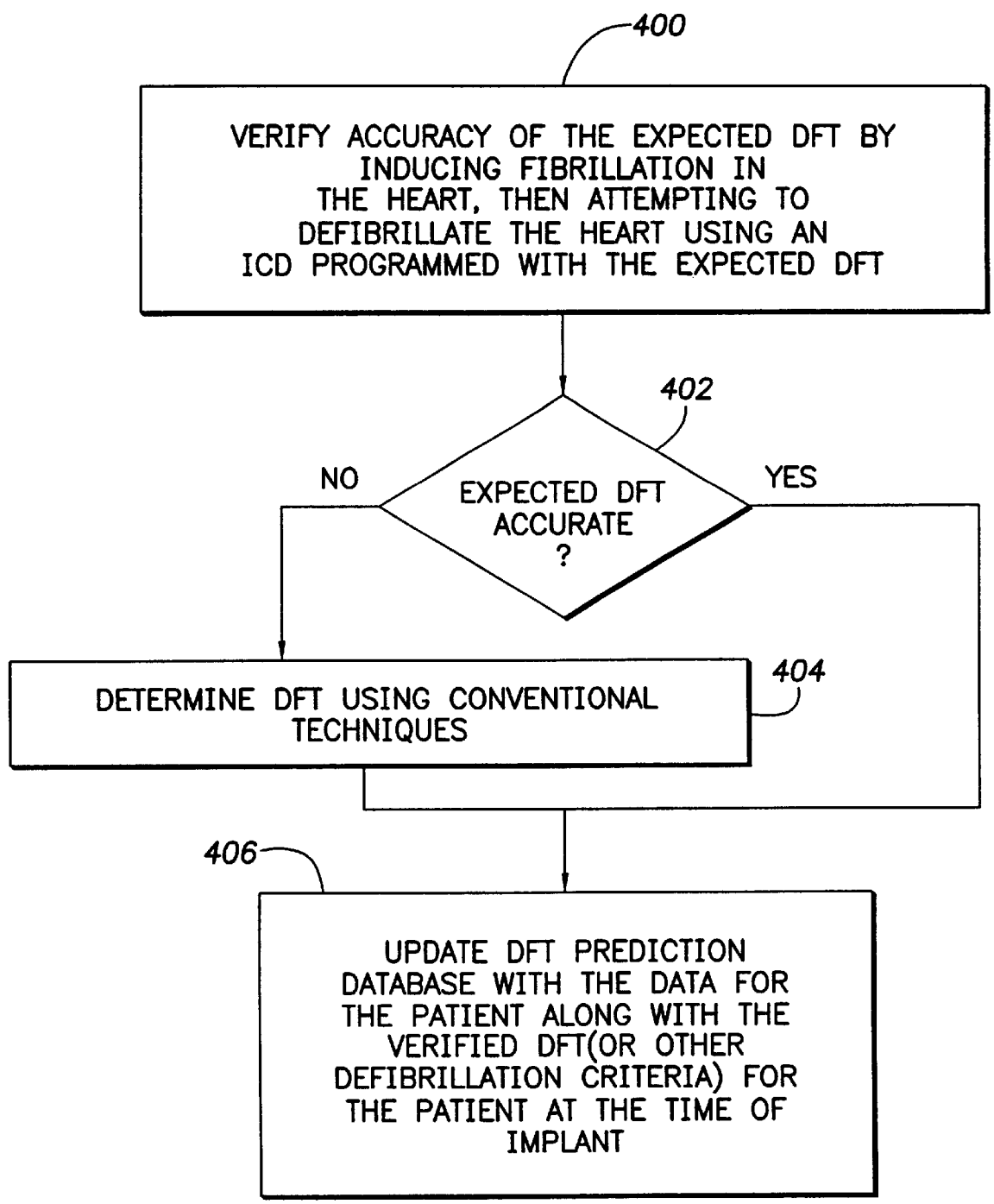

FIG. 4 illustrates a technique for verifying the accuracy of the expected DFT and for then updating the DFT prediction data base of FIG. 3 to include the data for the patient along with the expected DFT for the patient. As is shown in FIG. 4, once the DFT verification test has been completed, step 400, a determination is made at step 402 as to whether the DFT was accurate. If, in the unlikely event that the DFT was found to be inaccurate, step 404 is performed wherein conventional methods for DFT determination are employed to determine a correct value for the DFT. In either case, the DFT prediction database is then updated at step 406 to include the data for the particular patient as well as the DFT of the patient at the time of implant.

Referring again to FIG. 2, the substeps of step 102 of FIG. 1 performed to automatically determine the DFT for a particular patient using a DFT prediction database will now be described. At step 202, the programmer accesses a DFT prediction database which correlates patient clinical data for an entire population of patients with DFT. The DFT database is illustrated in FIG. 3. As can be seen, the database provides adjustment factors associated with each patient parameter, such as age, gender, medical history and the like. The adjustment factors are for use with an average patient DFT either stored within the DFT prediction database or stored separately within the programmer. The average DFT is preferably set to a value which, on the average, achieves an acceptable percentage of defibrillation success, such as 90%. In this regard, a value of ten joules may be stored as the average DFT. The adjustment factors provided within the database of FIG. 3 are percentage adjustment values for adjusting the average DFT. Different adjustment factors are provided for different ranges of the corresponding data. For example, several ranges of ages are stored along with a different age adjustment factors for each age range. Similar tables are provided for every other parameter. As far as age is concerned, there is a weak correlation among adults between increasing age and decreasing DFT. Other parameters which correlate with a lower DFT include a large ejection fraction and a history of cardiac arrest. Factors which correlate with an increased DFT include male gender, prior history of ventricular tachycardia (VT), large heart mass, large chest, and usage of any of the following drugs: Amiodarone (acute), Clofilium, Sotalol, and NAPA. Medications which correlate with a decreased DFT include: Encainide, ODE, Flecainide, Recainam, Amiodarone (chronic), and Atropine.

Figure 2:
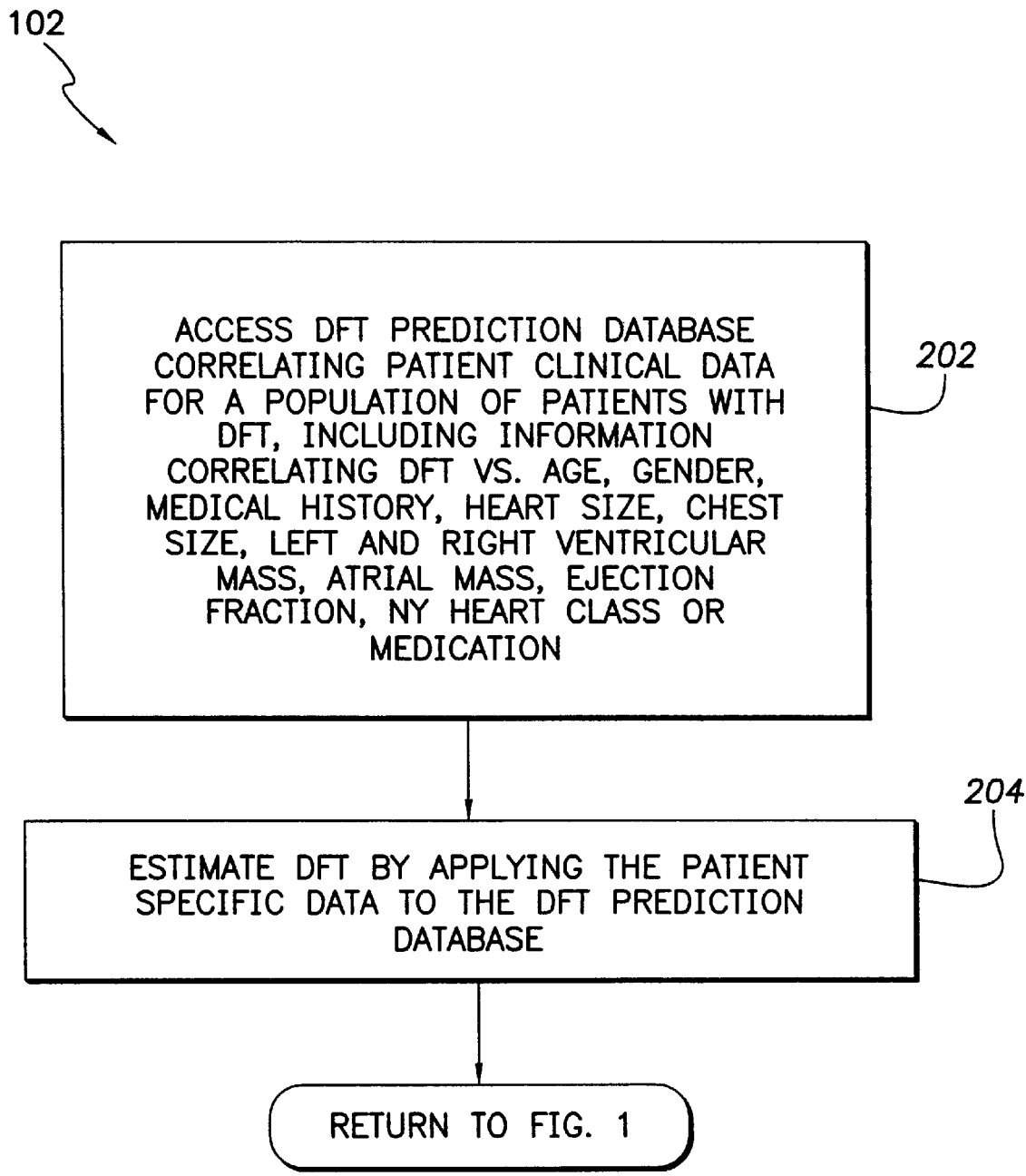

Then, at step 204 of FIG. 2, the programmer estimates the DFT for the patient by applying the patient data input at step 102 of FIG. 1 with the adjustment factors corresponding to those particular parameters of FIG. 3. Thus, the programmer increases or decreases the average DFT of ten joules by percentage amounts to determine an expected DFT for the patient. If less than a complete set of input patient parameters are provided, the programmer merely applies the parameters that have been input against corresponding portions of the database of FIG. 3 to approximate the DFT for the patient. The resulting DFT may be, for example, eight joules or perhaps fifteen joules depending upon the particular adjustment factors. The resulting estimated DFT for the patient is then displayed at step 104 of FIG. 1.

Thus, the DFT prediction database of FIG. 3 provides percentage adjustment factors for applying to an average DFT. In the alternative, the database may provide actual numeric values indicating, for example, a +0.1, +0.2, −0.1, −0.2 joule adjustment factors for various ranges of parameters. If so configured, the programmer merely adds and subtracts the numeric adjustment factors to the average DFT to yield the estimated DFT for the particular patient.

Regardless of the format for the adjustment factors, the programmer applies the adjustment factors to an average DFT obtained based upon a large number of patients. In the alternative, separate average DFT values may be stored for particular implantation configurations. For example, separate average DFT values may be provided for a non-thoracotomy lead configuration as opposed to an epicardial lead configuration. Likewise, different average DFT values may be stored for different ICD models. If so, then the adjustment factors of the dosage DFT prediction database are separately applied to each different average DFT value for each different implantation configuration and the resulting estimated DFT's for the patient are displayed, at step 104 of FIG. 1, along with the corresponding implantation configuration for which the DFT's were determined. As can be appreciated, a wide range of other specific configurations may be employed in accordance with the general principles of the invention.

Figure 5:
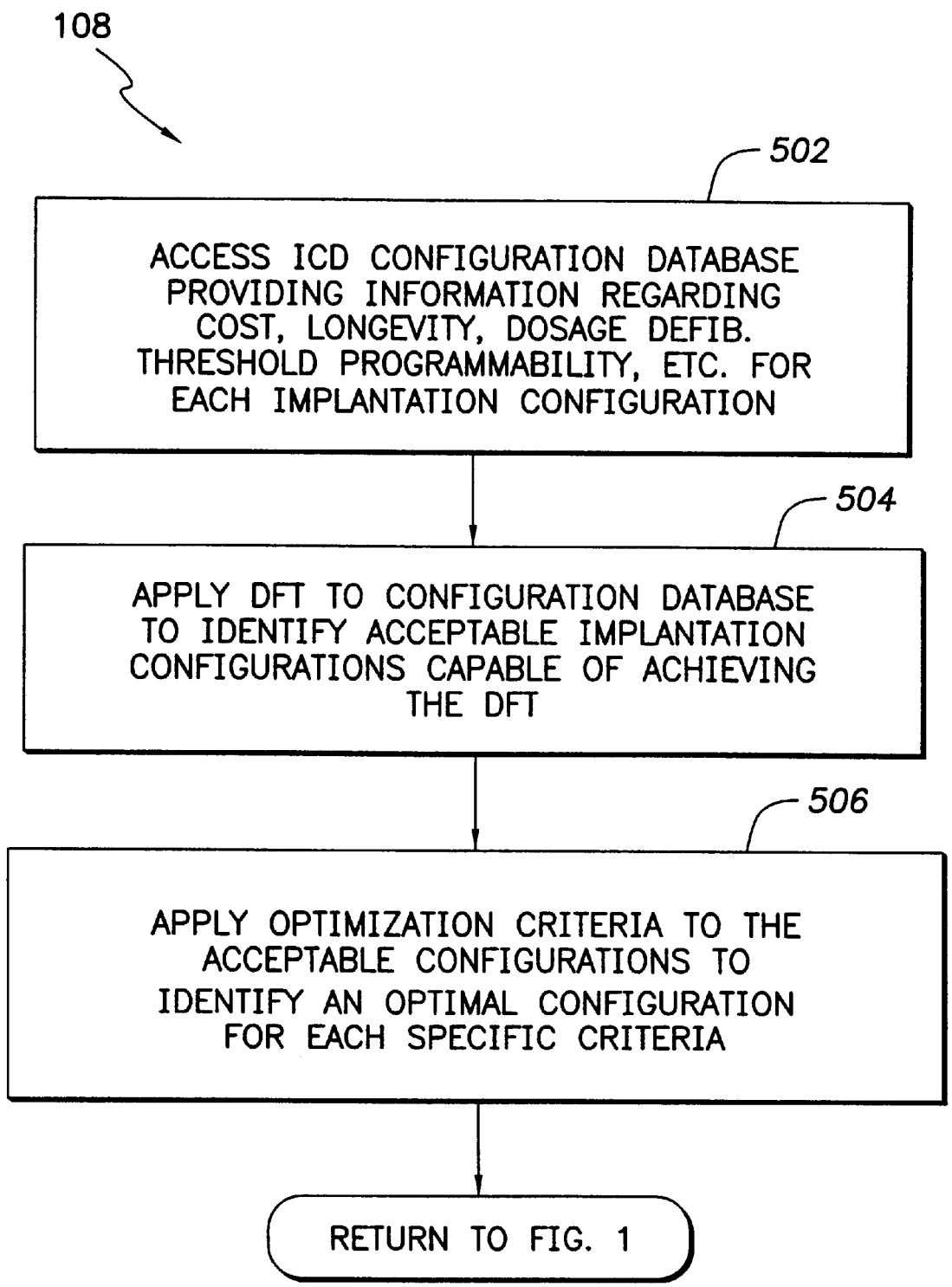

FIG. 5 illustrates substeps of step 108 of FIG. 1 performed to determine the optimal implantation configuration using an ICD implantation configuration database illustrated in FIG. 6. Initially, at step 502, the programmer accesses the configuration database of FIG. 6 which provides information for each of a set of predetermined implantation configurations pertaining to costs, expected longevity, programmable thresholds, and the like. As seen in FIG. 6, an exemplary implantation configuration may specify a particular ICD model, along with a lead type, a lead polarity, and an indication of whether an auxiliary wire is employed. For each such configuration, the database sets forth specific configuration parameters specifying the cost, the expected longevity, the amount of electrical energy per defibrillation pulse, the specific programmable thresholds, and the like. These parameters are initially determined from technical data provided by manufacturers and the like and stored within the programmer, maintained on a disk which is inserted into the programmer, or perhaps accessed from a centralized database stored on a central server.

At step 504 of FIG. 5, the programmer applies the DFT determined using the method of FIG. 2 to the configuration database of FIG. 6 to identify a set of acceptable implantation configurations capable of achieving the DFT. Thus, for example, if the DFT for the patient was determined to be 20 joules, but a particular configuration is capable of providing a maximum of 18 joules per pulse, then the particular configuration is deemed to be unacceptable. At step 506, the programmer then applies the optimization criteria (previously input by the physician at step 106 of FIG. 1) to the acceptable configurations to identify a particular optimal configuration. For example, if the physician selected overall cost as the optimization criteria, then the programmer compares the costs stored within the implantation configuration database for each acceptable configuration and selects the configuration having the lowest cost. On the other hand, if the physician selected device longevity as the optimization criteria, then the programmer examines the expected longevity values stored within the configuration database to identify the configuration providing the optimal longevity. The optimal and acceptable implantation configuration are displayed, as noted above, using the programmer for review by the physician.

Preferably, the configuration database of FIG. 6 specifically sets forth acceptable programmable DFT values for each configuration and the programmer selects the best programmable DFT value for each acceptable configuration. In other words, if a particular ICD model is capable of being programmed only to a resolution of two joules (such as ten joules, twelve joules, fourteen joules, etc.), then the programmer identifies the best programmable threshold for use with that configuration. Thus, in an example where the implantation configuration can be programmed to a resolution of two joules, if the DFT for the patient was determined to be thirteen joules, the programmer selects fourteen joules as the best DFT for use in programming the ICD.

If the dosage DFT prediction database is configured to provide separate adjustment factors for different implantation configurations, then the programmer, at step 504 of FIG. 5, correlates the separate DFT values with the particular implantation configurations stored within the configuration database of FIG. 6 to identify acceptable and optimal configurations. Thus, if the programmer previously determined that the dosage DFT for the patient is eight joules when using a configuration employing a non-thoracotomy lead only and ten joules when employing a configuration using the addition of a subcutaneous electrode, the programmer takes this information into account in identifying whether a particular configuration is acceptable or optimal.

Hence, FIGS. 1–6 illustrate a method for automatically determining a DFT for a particular patient and for automatically identifying acceptable and optimal implantation configurations capable of achieving the DFT. These determinations are made, in part, by correlating patient specific information with previously recorded information for an entire population of patients. The actual manner by which the programmer applies the patient data to the databases depends upon a particular programming of the programmer. In one example, the programmer employs fuzzy logic in making its determinations. As can be appreciated, a wide range of specific programming techniques may be employed consistent with the method steps thus far described. As numerous suitable programming techniques are well known, these techniques will not be described in further detail herein.

Figure 7:
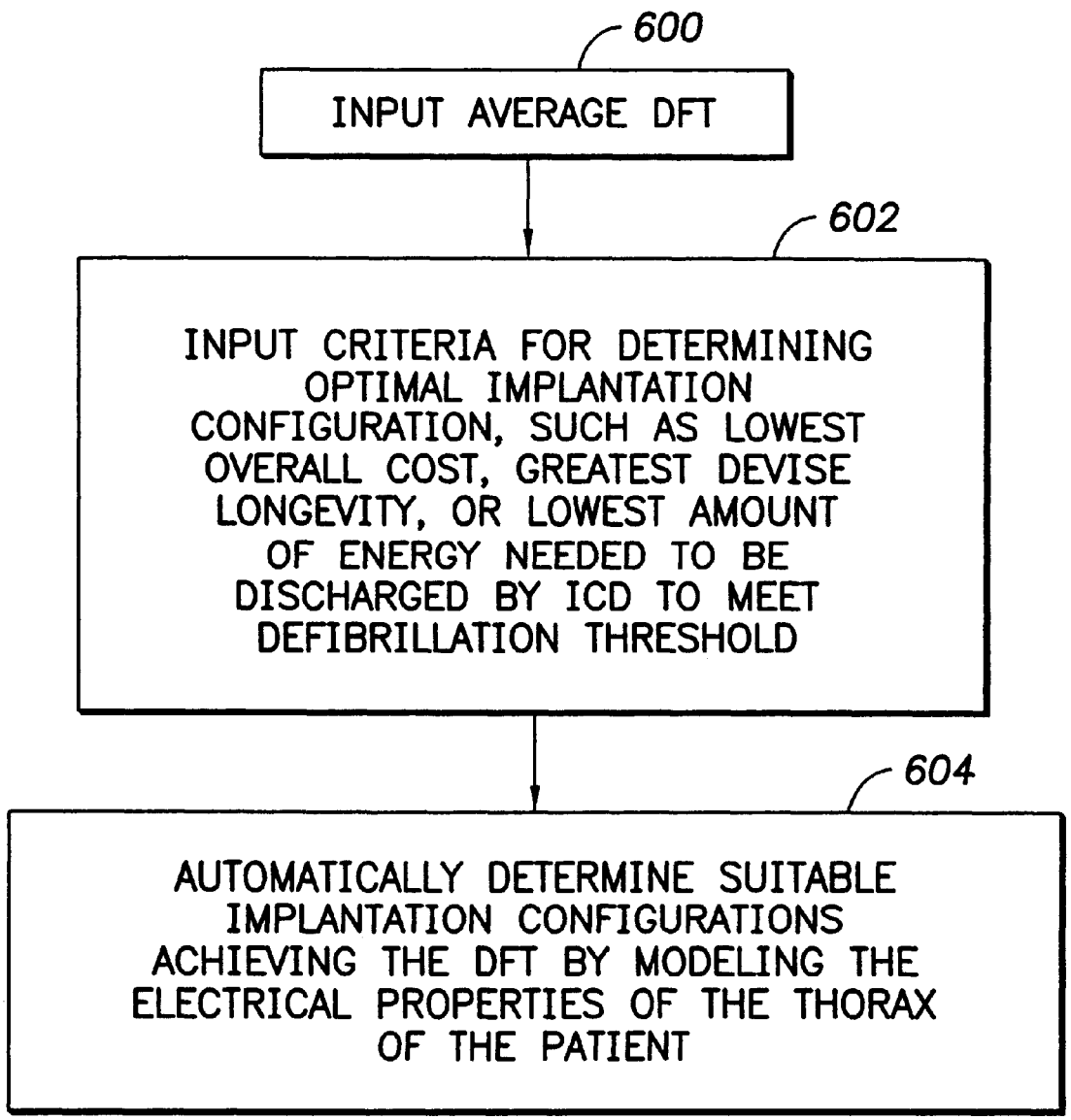
Figure 8:
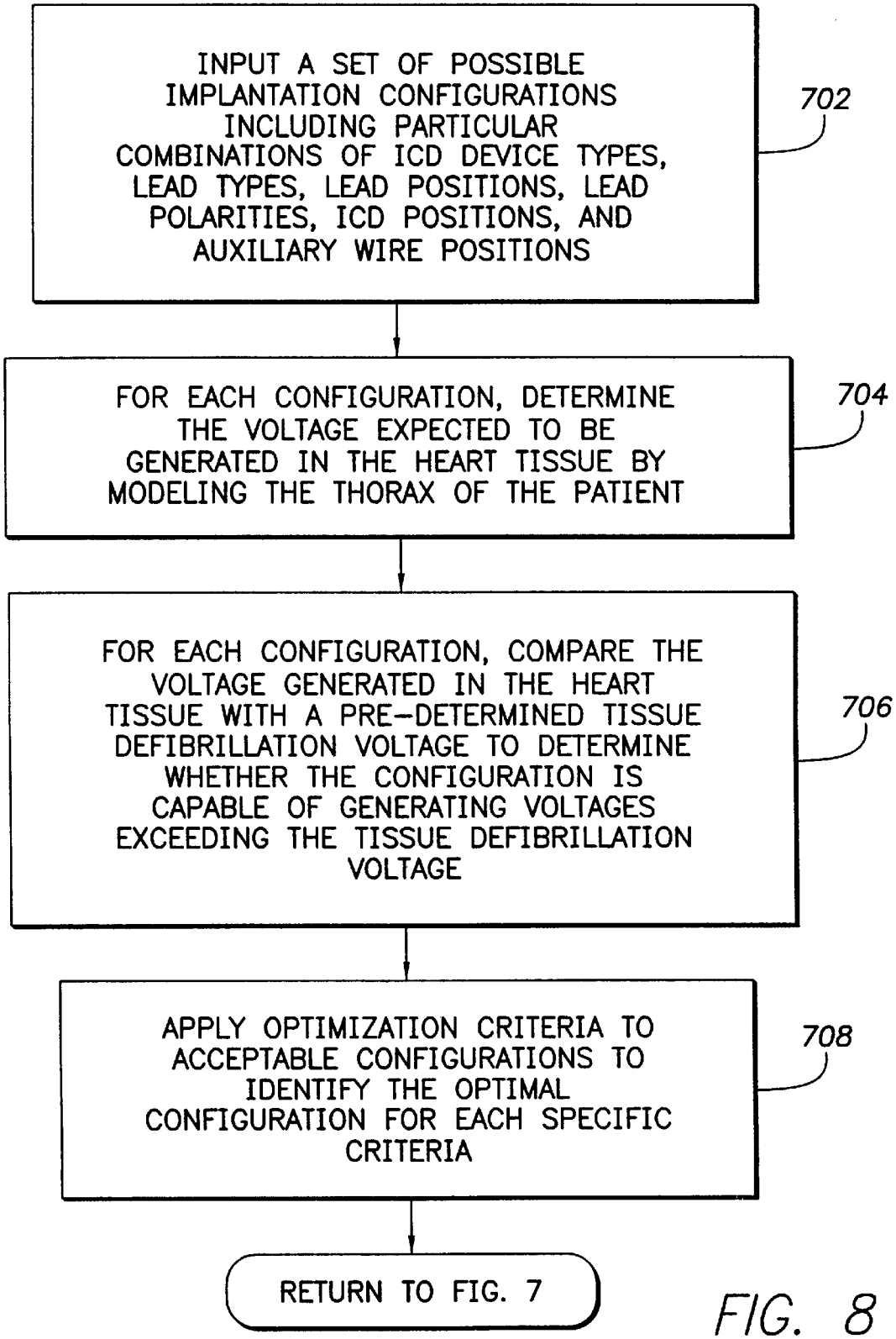
Figure 9:
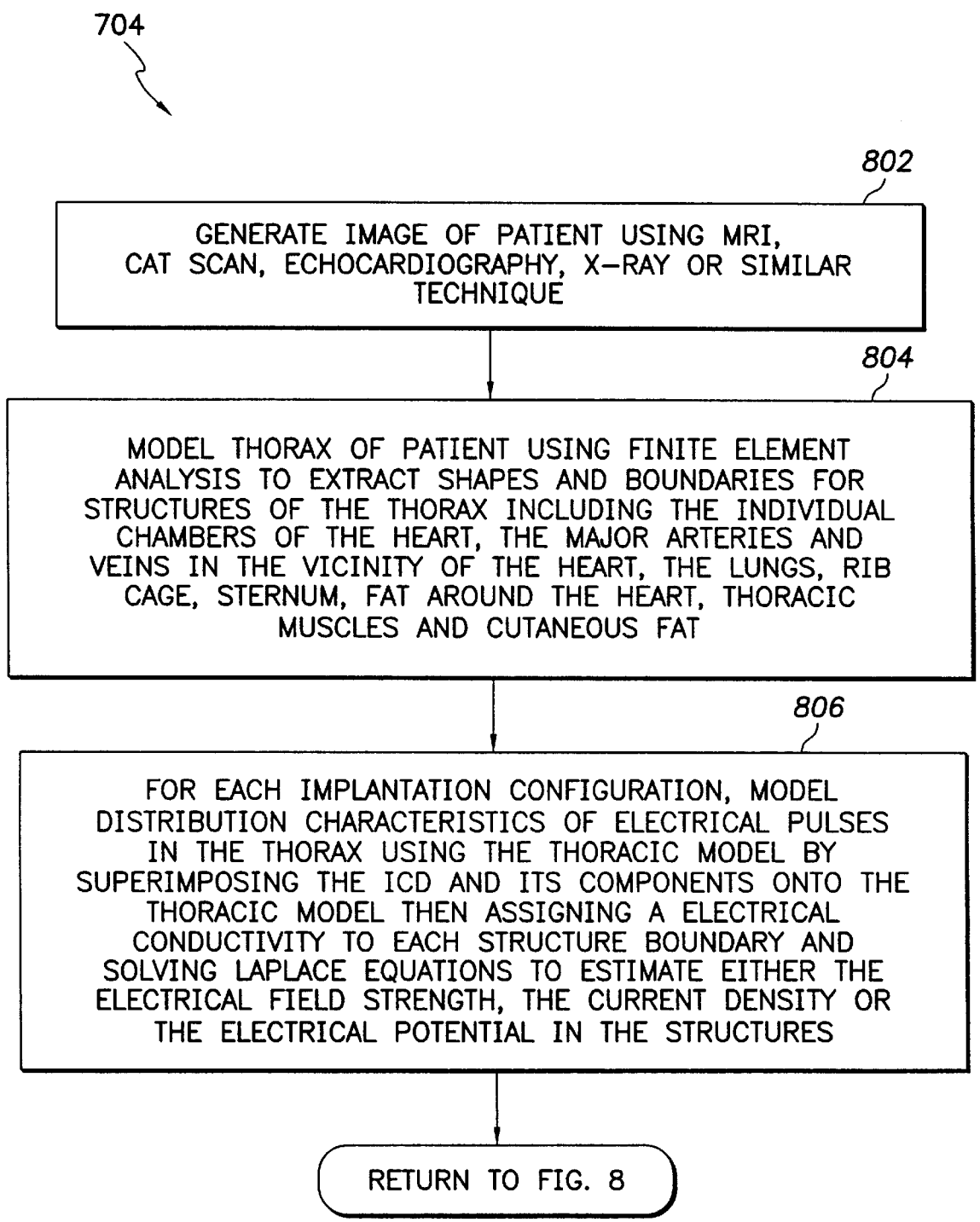

FIGS. 7–9 set forth a method for identifying acceptable and optimal implantation configurations for a particular patient by modeling electrical conduction properties of the thorax of the particular patient. Referring first to FIG. 7, at step 600 the programmer inputs an average tissue defibrillation criteria which may be, for example, in the range of 4.5–5.5 volts per centimeter for ninety-five percent of the heart tissue mass. As noted above, the tissue defibrillation threshold is the minimum electrical voltage gradient that must be induced within the muscle tissue of the heart to reliably defibrillate the tissue. This value is determined from available research data and stored within a database of the programmer or may be accessed from a central server. At step 602, the programmer permits the physician to select an optimization criteria.

Then, at step 604, the programmer automatically determines implantation configurations capable of generating an actual defibrillation voltage gradient in the heart of the patient exceeding the tissue defibrillation criteria by modeling the electrical properties of the thorax of the patient. Upon completion of step 604, the programmer displays a list of acceptable configurations, and a single optimal configuration, wherein each configuration is capable of administering a defibrillation pulse having a dosage sufficient to yield an actual defibrillation voltage in the heart of the patient greater than the tissue defibrillation criteria input at step 600. Thereafter, the physician merely elects the optimal configuration determined by the programmer or, in the alternative, selects one of the other acceptable configurations for implantation into the patient. Preferably, after the ICD is implanted, the physician conducts one fibrillation test to verify that the ICD is capable of adequately defibrillating the patient. Hence, as with the method of FIGS. 1–6, the method of FIGS. 7–9 eliminates the need to perform repeated cycles of fibrillation and defibrillation to determine the DFT and thereby overcomes the risks and costs associated therewith. The method of FIGS. 7–9 also permits an optimal ICD configuration to be determined prior to implant of an ICD within a patient.

FIG. 8 illustrates the steps of step 604 of FIG. 7 employed to determine the acceptable and optimal implantation configurations. Initially, at 702, the programmer inputs a set of possible implantation configurations including particular combinations of ICD device types, lead types, lead positions, lead polarities, ICD positions and auxiliary wire positions. To this end, a set of configurations similar to those employed in the database of FIG. 6 are input. The configurations are input from disk, or from a centralized database. At step 704, for each configuration, the programmer determines the voltage gradient or current density expected to be generated in the heart tissue of the patient by modeling the thorax of the patient. Once the voltage gradient or current density is determined, the programmer, at step 706, compares the voltage or current value with the tissue defibrillation criteria (input at step 600 of FIG. 7) to determine whether the configuration is capable of exceeding the issue defibrillation criteria. Thus, if the programmer determines at step 704 that a particular configuration will generate only 2.8 volts per centimeter for 95% of the heart tissue mass, then at step 706 the programmer determines that the configuration is unacceptable. Because the tissue defibrillation voltage depends, in part, upon any medications that may be taken by the patient, an identification of any medications that the patient is taking are preferably input into the programmer for use in identifying acceptable implantation configurations.

At step 708, the programmer applies the optimization criteria previously selected by the physician to identify one configuration out of all of the acceptable configurations which best achieves the optimization criteria. For example, if ten different configurations are capable of achieving the 5.0 volt per centimeter tissue defibrillation voltage, and the physician selected longevity as the optimization criteria, then the programmer, at step 708, accesses a configuration database, such as the database of FIG. 6, to identify the configuration providing the greatest longevity.

FIG. 9 illustrates the steps performed in connection with step 704 of FIG. 8 to determine the current or voltage in the heart of the patient. At step 802, an image of the thorax of the patient is input to the programmer. The image is, for example, generated using an MRI, CAT scan, echocardiography, X-ray or similar technique. Depending upon the particular imaging technique, the image is input in digital form or may first need to be digitized by the programmer. In any case, at step 804, the programmer generates a model of the thorax of the patient using finite element analysis to extract shapes and boundaries for each structure of the thorax. In a specific implementation, the programmer extracts the shapes and boundaries for each of the four chambers of the heart, the major arteries and veins in the vicinity of the heart, the lungs, rib cage, and sternum. Additionally, the programmer may also extract the shapes and boundaries for fat around the heart, thoracic muscles and cutaneous fat. Finite element analysis techniques are well known in the art and accordingly will not be described in detail herein.

Hence, following step 804, the programmer stores an internal digital representation of the major structures of thorax of the individual patient. Importantly, the digital representation is unique to the particular patient and is representative of the internal structures of the thorax of the patient. Hence, if the patient has a particularly large heart, then the digital representation will be representative thereof. If the patient has a large amount of fat in the vicinity of the heart, then, again, the digital representation identifies same.

Next, at step 806, for each possible implantation configuration input at step 702 of FIG. 8, the programmer models conduction characteristics of electrical pulses in the thorax by superimposing the ICD and its components onto the thoracic model generated at step 804, then assigning an electrical conductivity value to each structure boundary and solving Laplace's equations to estimate the current or voltage in the heart. The current or voltage values may be represented, for example, in terms of electrical field strength, current density or electrical potential within the individual structures of the heart. The Laplace equations solved by the programmer are as follows:

$$\nabla \cdot (\sigma \nabla \Phi) = 0 \qquad (1)$$

$$\frac{\partial \Phi}{\partial \eta} = 0 \qquad (2)$$

on the outside surface of the body
(Neumann Boundary Condition)

$$\Phi = 1 \qquad (3)$$

on the anode electrode
(Dirichlet Boundary Conditions)

$$\Phi = 0 \qquad (4)$$

on the cathode electrode
(Dirichlet Boundary Conditions)

Equation 1 is the governing equations for the unknown potentials $\Phi$ in the body due to the defibrillation shock. Equations 2–4 are the conditions that are known and that specify the unique solution to the problem. Briefly, equation (2) states that no current can exit the body (the surrounding air is a dielectric). Equation 3 and 4 specifies a normalized potential on each electrode as either 1 V for the anode or 0 V for the cathode. Since this problem is linear, the solution can be scaled for the actual voltage on each electrode; i.e., if an actual potential difference of 450 V is going to be applied on the electrodes, then the solution from the normalized problem can be multiplied by 450.

Once the programmer has completed the computations, then it predicts the current pathways in the thorax for a given electrode system. The solution specifies the electric field, current density and potential everywhere in the thorax, including the heart.

Following completion of step 806, the programmer has thereby determined specific voltage gradient or current density values expected to be generated within the heart of the patient for each of the specific implantation configuration. For implantation configurations employing ICD's that can be programmed to output different pulses of different energies, the programmer determines the resulting voltage or current for each different programmable pulse energy value. As noted above, each of the current and voltage values are then compared with the tissue defibrillation voltage input at step 600 to determine whether the tissue defibrillation voltage would be exceed by the actual defibrillation voltage generated in the heart. If not, the configuration is deemed unacceptable. Acceptable configurations are further examined to identify one optimal configuration based upon the optimization criteria input by the physician. Note that, for programmable ICD's, some-specific programmable pulse energy values may be unacceptable whereas others may be acceptable. This information is taken into account by the programmer during the optimization of step 604 of FIG. 7, as needed. The resulting display presented to the physician of the optimal and acceptable implantation configurations additionally indicates the recommended programming value for the ICD and further indicates if any programmable values are unacceptable.

Thus, FIGS. 7–9 illustrate a technique for determining an optimal ICD implantation configuration and a DFT for use therewith, based entirely upon a model of the thorax of the patient. Depending upon the computing power of the programmer, the actual modeling of the thorax of the patient is performed by the programmer itself or is performed by a separate computer, perhaps a centralized computer accessible by a large number of ICD programmers. The actual amount of processing power required depends upon the degree of resolution of the thorax model and upon the number and size of the structures involved. Depending upon the implementation, the model may be restricted to modeling only the heart and immediate vicinity. In other implementations, the model encompasses the entire thorax or perhaps the entire body of the patient.

Depending upon the resolution employed and upon the reliability of the input parameters such as the conductivity of each structure, the technique of FIGS. 7–9 can very precisely determine the minimum amount of electrical pulse energy that needs to be generated by an ICD to generate an actual defibrillation voltage in the heart exceeding the tissue defibrillation voltage for the particular patient. Accordingly, very precise optimization may be achieved and a very low DFT safety margin may be employed. Moreover, device longevity may be greatly enhanced over techniques which require a very large safety margin for use in programming an ICD.

Hence, FIGS. 1–6 provide a technique which determines the expected DFT for patient and identifies acceptable implantation configurations based upon predictive databases. FIGS. 7–9 provide a technique for determining DFT and acceptable implantation configurations by modeling the thorax of the patient. If desired, a combination of these two techniques may be employed to further enhance the accuracy and reliability of the resulting determinations. For example, both techniques may be applied simultaneously with the resulting DFT values averaged together. Alternatively, if the thorax model is set to a resolution sufficient to determine the DFT to a high precision, the resulting value may be used to enhance the accuracy of predictive databases by updating the adjustment values of the predictive databases (FIG. 3 and FIG. 6) accordingly. Hence, even if the modeling technique is not used in connection with each individual patient, perhaps because of computing costs and associated time delays, the modeling technique may nevertheless be helpful to improve the accuracy of the predictive databases by more precisely correlating adjustment factors with ranges of patient parameters.

What has been described are various techniques for determining DFT's for use with an ICD to be implanted into a patient and for further determining acceptable and optimal implantation configurations sufficient to satisfy the DFT. The embodiments described herein are merely exemplary of the invention and should not be construed as limiting the scope of the invention. Rather, general principles of the invention can be applied to a wide variety of implantable medical devices to determine a wide variety of programmable values or configurations. Principles of the invention may be applied to the determination of other programmable values for an ICD besides DFT or to determine programmable values for pacemakers. In this regard, the general techniques described herein in connection with modeling the thorax of the patient may be exploited in a wide variety of circumstances in connection with pacemakers, ICD's and other implantable medical devices. Moreover, for devices to be implanted into other portions of the human anatomy, the modeling techniques may be applied to the appropriate portion of the patient and are therefore not limited to modeling the thorax of the patient.

Components of a programmer for use in implementing the steps of the method may be implemented using any appropriate technology including software running on a generally programmable computer, or dedicated logic hardwired into an application specific integrated circuit (ASIC) or the like.

What is claimed is:

1. A system for determining a defibrillation threshold for a particular patient, the system comprising:

means for storing predictive information within a database correlating patient clinical data with defibrillation thresholds for a population of patients;

means for acquiring patient data for a particular patient; and means for automatically determining the defibrillation threshold for the particular patient based upon the data for the particular patient in combination with the information correlating patient clinical data with defibrillation thresholds; and means for updating the database to include patient data and the defibrillation threshold for the particular patient.

2. The system of claim 1, further comprising:

means for testing the defibrillation threshold for the particular patient to verify that it is accurate and, if it is not, determining a new defibrillation threshold by repeatedly fibrillating then defibrillating the particular patient's heart using defibrillation pulses of differing energy.

3. A system for determining a defibrillation threshold for a particular patient and for also determining an implantation configuration for an implantable cardioverter defibrillator (ICD) for implant within the patient, the system comprising:

means for storing predictive information within a database correlating patient clinical data with defibrillation thresholds for a population of patients;

means for acquiring patient data for a particular patient;

means for automatically determining the defibrillation threshold for the particular patient based upon the data for the particular patient in combination with the information correlating patient clinical data with defibrillation thresholds;

means for storing predictive information correlating ICD implantation configurations with defibrillation thresholds for the population of patients; and means for automatically determining an implantation configuration capable of providing defibrillation pulses achieving the defibrillation threshold for the particular patient based on the determined defibrillation threshold for the particular patient in combination with the information correlating ICD implantation configurations with defibrillation thresholds for the population of patients.

4. The system of claim 3, wherein the means for automatically determining the implantation configuration comprises:

means for imaging the thorax of the particular patient;

means for inputting parameters defining a plurality of ICD implantation configurations; and means for automatically determining, from the image of the particular patient in combination with the implantation configuration parameters, the ICD implantation configurations sufficient to provide defibrillation pulses exceeding a defibrillation threshold of the particular patient by a predetermined safety margin.

5. The system of claim 3, wherein the means for automatically determining the implantation configuration comprises:

means for imaging the thorax of the particular patient;

means for inputting parameters defining the ICD and lead implantation configuration; and means for automatically determining, from the image of the particular patient in combination with the implantation configuration parameters, whether the ICD implantation configuration is sufficient to provide defibrillation pulses exceeding a defibrillation threshold of the patient by a predetermined safety margin.

6. A system for determining a defibrillation threshold for a particular patient and for also determining an implantation configuration for an implantable cardioverter defibrillator (ICD) for implant within the patient, the system comprising:

a defibrillation threshold information storage unit for storing predictive information correlating patient clinical data with defibrillation thresholds for a population of patients;

an acquisition system for acquiring patient data for a particular patient;

a defibrillation threshold determination unit for determining the defibrillation threshold for the particular patient based upon the data for the patient in combination with the information correlating patient clinical data with defibrillation thresholds;

an implantation configuration storage unit for storing predictive information correlating ICD implantation configurations with defibrillation thresholds for a population of patients; and an implantation configuration deternmination unit for automatically determining an implantation configuration capable of providing defibrillation pulses exceeding the defibillation threshold based on the predicted defibrillation threshold for the particular patient in combination with the information correlating ICD implantation configurations with defibrillation thresholds.

7. A system for determining a defibrillation threshold for a particular patient, the system comprising:

a defibrillation threshold information storage unit for storing predictive information correlating patient clinical data with defibrillation thresholds for a population of patients;

an acquisition system for acquiring patient data for a particular patient;

a thorax imaging unit for imaging the thorax of the patient;

a thorax modeling unit for modeling the thorax of the patient based upon images of the patient to generate a patient model specifying a default electrode size, shape and position;

an electrical pulse modeling unit for modeling distribution characteristics of electrical pulses in the patient based upon the patient model; and a defibrillation threshold determination unit for determining the defibrillation threshold based upon the data for the patient in combination with the information correlating patient clinical data with defibrillation thresholds and also based on the distribution characteristics of electrical pulses in the patient and defibrillation criteria.

8. A method, performed by a programming device operative to program the operation of an implantable cardioverter defibrillator (ICD), for determining a defibrillation threshold for a particular patient, the method comprising:

accessing predictive information correlating patient clinical data with defibrillation thresholds for a population of patients;

acquiring patient data for the particular patient;

automatically determining the defibrillation threshold for the particular patient based upon the patient data for the particular patient in combination with the information correlating patient clinical data with defibrillation thresholds;

accessing predictive information correlating ICD implantation configurations with defibrillation thresholds for the population of patients; and automatically determining an implantation configuration capable of providing defibrillation pulses exceeding the defibrillation threshold for the particular patient based on the determined defibrillation threshold for the particular patient and the information correlating ICD implantation configurations with defibrillation thresholds for the population of patients.

9. A method for determining a defibrillation threshold for a particular patient and for also determining an implantation configuration for an implantable cardioverter defibrillator (ICD) for implant within the patient, the method comprising:

accessing predictive information correlating patient clinical data with defibrillation thresholds for a population of patients;

acquiring patient data for the particular patient;

automatically determining the defibrillation threshold for the particular patient based upon the patient data for the particular patient in combination with the information correlating patient clinical data with defibrillation thresholds;

acquiring thorax imaging data of the particular patient's thorax;

acquiring parameters defining a plurality of ICD implantation configurations; and automatically determining, from the imaging data of the particular patient in combination with the implantation configuration parameters, ICD implantation configurations sufficient to provide defibrillation pulses exceeding the defibrilation threshold of the particular patient by a predetermined safety margin.

10. The method of claim 9, wherein automatically determining the ICD implantation configurations sufficient to provide defibrillation pulses exceeding the defibrillation threshold determined based on patient data comprises predicting the defibrillation threshold for the particular patient based on distribution characteristics of electrical pulses in the particular patient.

11. The method of claim 10, wherein predicting the defibrillation threshold based on distribution characteristics of electrical pulses in the particular patient comprises:

modeling the particular patient's thorax based upon the thorax imaging data to generate a patient model;

modeling distribution characteristics of electrical pulses in the particular patient based upon the patient model;

specifying defibrillation electrode size, shape and position; and predicting the defibrillation threshold based on the distribution characteristics of electrical pulses in the particular patient and a defibrillation criteria.

12. The method of claim 11, wherein modeling the thorax of the patient is performed to extract a shape and boundary of a plurality of structures in the thorax.

13. The method of claim 11, wherein modeling the thorax of the patient is performed to extract a shape and boundary of a plurality of structures in the thorax including at least individual chambers of the patient's heart and major arteries and veins in the vicinity of the patient's heart.

14. The method of claim 11, wherein modeling the thorax of the patient is performed to extract a shape and boundary of a plurality of structures in the thorax including one or more of the patient's lungs, rib cage, sternum, fat around the patient's heart, thoracic muscles, and cutaneous fat.

15. The method of claim 11, wherein acquiring ICD implantation configuration parameters comprises:

displaying a graphic representation of the model of the patient;

displaying a graphic representation of a default combination of ICD implantation configuration parameters including a default position of electrode leads; and providing user modifications to the default combination of ICD implantation configuration parameters.

16. The method of claim 11, wherein modeling distribution characteristics of electrical pulses in the patient comprises:

assigning an electrical conductivity to each structure boundary; and solving differential equations representative of electrical conduction characteristics to estimate one or more of electrical field strength, current density, and electrical potential within at least a portion of the patient.

17. The method of claim 16, wherein determining the defibrillation threshold is performed based on the estimates of one or more of the electrical field strength, the current density, and the electrical potential.

18. The method of claim 17, wherein the defibrillation threshold is estimated based on criteria specifying that a certain percentage of heart mass must experience an electrical field of at least a certain number of volts per centimeter.

19. The method of claim 17, wherein the defibrillation threshold is estimated based on criteria specifying that a 95% of heart mass must experience an electrical field of at least a 3–6 volts per centimeter.

20. The method of claim 9, further comprising:

acquiring information representative of medicines expected to be taken by the patient; and wherein automatically determining whether the ICD configuration is sufficient to provide defibrillation pulses achieving a defibrillation threshold of the particular patient additionally takes into account any medicines expected to be taken by the particular patient.

\* \* \* \* \*